(12) United States Patent
Takami

(10) Patent No.: US 7,130,048 B2
(45) Date of Patent: Oct. 31, 2006

(54) METHOD AND APPARATUS FOR FORMING SUBSTRATE FOR SEMICONDUCTOR OR THE LIKE

(75) Inventor: Yoshio Takami, Yokohama (JP)

(73) Assignee: Advanced LCD Technologies Development Center Co., Ltd., Yokohama (JP)

(*) Notice: Subject to any disclaimer, the term of this patent is extended or adjusted under 35 U.S.C. 154(b) by 400 days.

(21) Appl. No.: 10/717,552

(22) Filed: Nov. 21, 2003

(65) Prior Publication Data

US 2004/0105096 A1 Jun. 3, 2004

(30) Foreign Application Priority Data

Nov. 25, 2002 (JP) ............... 2002-341330

(51) Int. Cl.
*G01J 4/00* (2006.01)

(52) U.S. Cl. .................................... 356/369

(58) Field of Classification Search ........... 356/369, 356/632; 250/207, 225, 214 VT
See application file for complete search history.

(56) References Cited

U.S. PATENT DOCUMENTS

| | | | | |
|---|---|---|---|---|
| 4,141,780 | A | * | 2/1979 | Kleinknecht et al. ......... 117/85 |
| 4,431,914 | A | * | 2/1984 | Mourou et al. .......... 250/214 R |
| 4,891,581 | A | * | 1/1990 | Takiguchi ..................... 324/96 |
| 6,782,337 | B1 | * | 8/2004 | Wack et al. ................. 702/155 |

OTHER PUBLICATIONS

Mutsuko Hatano, et al., "Excimer laser-induced temperature field in melting and resolidification of silicon thin films", Journal of Applied Physics, vol. 87, No. 1, Jan. 1, 2000, pp. 36-43.

* cited by examiner

*Primary Examiner*—Gregory J. Toatley, Jr.
*Assistant Examiner*—Isiaka O. Akanbi
(74) *Attorney, Agent, or Firm*—Oblon, Spivak, McClelland, Maier & Neustadt, P.C.

(57) ABSTRACT

In an apparatus which determines characteristics of a thin film according to the present invention, a temporal change in a refractive index n and an extinction coefficient k of a thin film in a period from start of a change in the thin film as a processing target (e.g., melting) to end of the change (e.g., solidification) can be obtained with a high time resolution of pico-seconds. Based on this, it is possible to know a progress of a change in state of the thin film (e.g., crystallization) or a transition of growth of crystal grains in units of pico-seconds.

13 Claims, 7 Drawing Sheets

METHOD AND APPARATUS FOR FORMING SUBSTRATE FOR SEMICONDUCTOR OR THE LIKE

CROSS-REFERENCE TO RELATED APPLICATIONS

This application is based upon and claims the benefit of priority from the prior Japanese Patent Application No. 2002-341330, filed Nov. 25, 2002, the entire contents of which are incorporated herein by reference.

BACKGROUND OF THE INVENTION

1. Field of the Invention

The present invention relates to a method and an apparatus for determining characteristics of a semiconductor thin film.

2. Description of the Related Art

For example, in regard to manufacture of a thin film transistor for a switching element of, e.g., a liquid crystal display apparatus or an organic electroluminescence display apparatus, M. Hatano, S. Moon, M. Lee and K. Suzuki, (C. P. Grigoropoulos), Journal of Applied Physics, vol. 87, No. 1, 2000, pp, 36 to 43, Excimer Laser-Induced Temperature Field in Melting and Resolidification of Silicon Thin Films reports a method by which an annealed position provided to an amorphous silicon thin film is irradiated with a monitor light ray and an intensity of its reflected light is detected, thereby determining characteristics of the thin film.

The above cited reference mentions that the reflected light of the monitor light from the silicon thin film is detected by, e.g., a silicon PN junction photodiode type photodetector which has a response time of 1 nano-second (which will be denoted as "ns" hereinafter), i.e., a time resolution of 1 ns, and a temporal change of a detection signal waveform is measured by a sampling oscilloscope which samples a frequency signal of 1 GHz.

The silicon thin film is molten by laser irradiation for several-ten to 100 nm and crystallized in a subsequent solidification process, and a growth of crystal grains is generated. As a result, the silicon thin film varies from the amorphous type to the polycrystal type. A time required from melting to end of solidification is several-hundred ns.

The silicon thin film is affected to have metallic properties due to melting, an extinction coefficient k is increased, a reflected light intensity is thereby increased, the extinction coefficient k is decreased due to solidification after melting, and the reflected light intensity is thereby decreased. The temporal change of the reflected light intensity of the silicon thin film during melting or solidification is detected by the photodetector, the characteristics of the thin film are determined, and the crystallinity of the thin film is evaluated based on the characteristics.

However, in the method described in the above cited reference, only one set of information is obtained every 1 ns with respect to the reflected light intensity.

For example, a time of melting, a reflection factor or a transmittance is obtained from this one set of information, and it is thus difficult to determine important optical characteristics of the thin film such as a refractive index or an extinction coefficient in order to evaluate a degree of progress that the thin film is crystallized.

Further, it is substantially impossible to measure a change in the reflected light intensity concerning a melting-solidification process of several-hundred ns, i.e., a degree of progress that the thin film is crystallized with a time resolution higher than 1 ns.

Therefore, the characteristics of the thin film cannot be correctly specified in the prior art, and there is known that a defect of, e.g., electrical characteristics is generated in a liquid crystal display apparatus or the like using as a switching element a thin film transistor having an unsurely evaluated thin film.

BRIEF SUMMARY OF THE INVENTION

It is an object of the present invention to provide a method and an apparatus which detect a state of a thin film at a high speed in order to determine characteristics of a semiconductor thin film.

According to an aspect of the present invention, there is provided a method for determining characteristics of a thin film, comprising: irradiating with a monitor light ray at least a position of a processing target which is irradiated with a light energy which can perform predetermined processing or finishing; detecting a reflected light ray generated from the processing target by the monitor light ray by a light sensing mechanism having a plurality of substantially continuous light sensing elements; and measuring a temporal change in an angle distribution of an intensity of the reflected light detected by the light sensing mechanism.

According to another aspect of the present invention, there is provided an apparatus for specifying a processing state and/or a finishing state of a processing target, comprising: a monitor light generation device which can irradiate with a monitor light ray at least a position of a processing target which is irradiated with a light energy which can perform predetermined processing or finishing; a light sensing mechanism which detects a reflected light ray generated from the processing target irradiated with the monitor light ray, and detects electrons corresponding to the reflected light ray and/or a light ray obtained by converting the electrons corresponding to the reflected light ray; and a reflected light measurement mechanism which measures a temporal change in an angle distribution of an intensity of the reflected light ray detected by the light sensing mechanism.

According to still another aspect of the present invention, there is provided an apparatus for determining characteristics of a thin film, comprising: a monitor light irradiator which irradiates a monitor light ray having a polarization light in a direction of the polarization light is a predetermined direction, and the monitor light ray is condensed on the thin film through a lens system; and a light measurement device which receives a reflected light ray of the monitor light ray from the thin film, has a light sensing surface having a plurality of substantially continuous light sensing elements, and measures a temporal change in an angle distribution of an intensity of the reflected light ray.

According to further another aspect of the present invention, there is provided an apparatus for determining characteristics of a thin film, comprising: a monitor light irradiator which irradiates a monitor light ray having at least one of the S polarization light and the P polarization light, and the monitor light ray is condensed on the thin film through a lens system; and a light measurement device which receives a reflected light ray of the monitor light ray from the thin film, has a light sensing surface having a plurality of substantially continuous light sensing elements, and measures a temporal change in an angle distribution of an intensity of the reflected light ray.

According to still further another aspect of the present invention, there is provided a method for determining characteristics of a thin film, comprising: irradiating with a monitor light ray includes a polarization light in a direction of the polarization is a predetermined direction which is irradiated with a light energy which can perform predetermined processing or finishing; detecting a reflected light ray generated from the processing target by the polarization light of the monitor light ray by a light sensing mechanism having a plurality of substantially continuous light sensing elements; and measuring a temporal change in an angle distribution of an intensity of the reflected the light detected by the light sensing mechanism.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment according to the present invention will now be described hereinafter with reference to the accompanying drawings.

Figure 1:
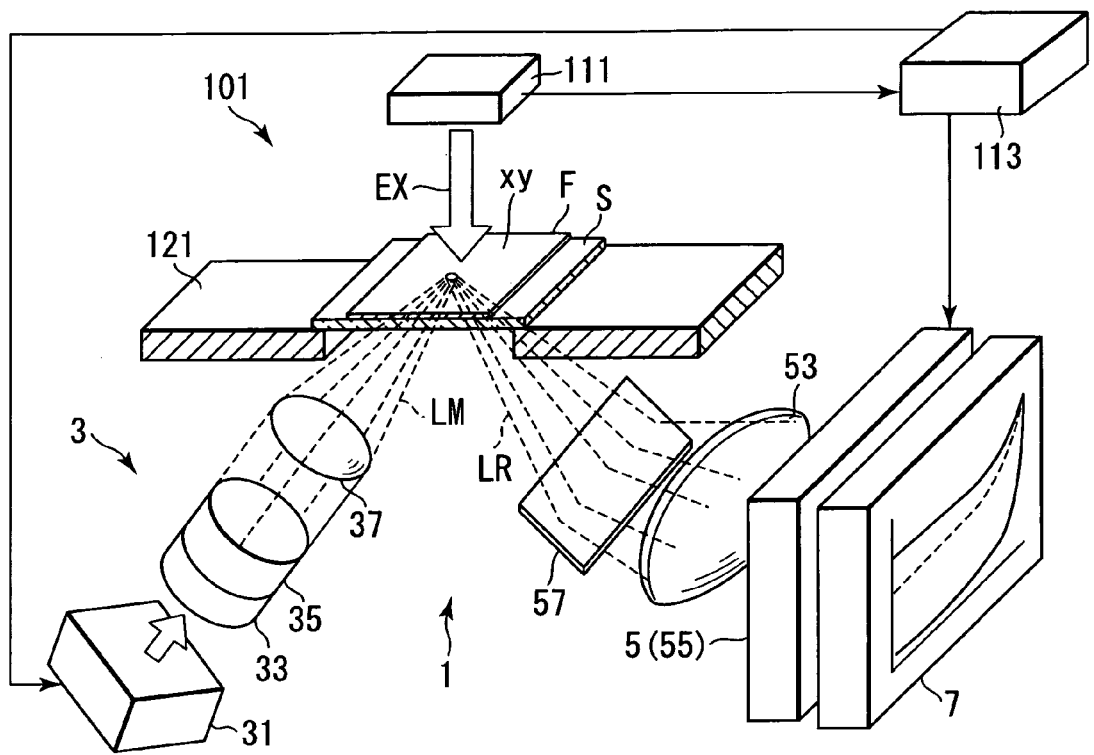
FIG. 1 is a schematic view illustrating a laser annealing apparatus which is an example of a substrate finishing/processing apparatus in which an apparatus which determines characteristics of a semiconductor thin film is incorporated according to an embodiment of the present invention.

FIG. 1 shows an example of a laser annealing apparatus as an example of a substrate finishing/processing apparatus in which an apparatus which determines characteristics of a semiconductor thin film according to an embodiment of the present invention is incorporated.

The apparatus 1 which determines characteristics of a semiconductor thin film is integrally incorporated at a predetermined position of, e.g., a laser annealing apparatus 101 which is an example of a substrate finishing/processing apparatus holding a substrate S as a target whose characteristics should be determined for finishing/processing, which is a rear surface side of the substrate S in the example of FIG. 1. It is to be noted that each of the apparatus 1 which determines characteristics of the thin film and the laser annealing apparatus 101 is operated in a vacuum container in which a pressure is decreased to a predetermined degree of vacuum or substituted by an atmosphere although not shown.

The laser annealing apparatus 101 includes a laser beam source device 111 for annealing and an XY stage drive mechanism (not shown) which moves a sample base 121 which detachably holds a substrate S having a thin film F formed thereto in two directions orthogonal to each other. It is to be noted that only a part of the sample base 121 is shown in the example of FIG. 1. Further, in the laser beam source device 111, a time adjustment device (timing notification mechanism) 113 which can set a timing to generate a laser beam by the laser beam source device 111, a timing to emit a monitor light ray and a timing to operate a streak camera which will be described later with reference to FIG. 2 is connected to a monitor light source device 31 of a later-described apparatus 1 which determines characteristics of a thin film. That is, the timing with which a later-described monitor laser beam LM is emitted is set to a predetermined timing by the time adjustment device (timing notification mechanism) 113 with respect to a time at which the annealing laser beam is outputted from the laser beam source device 111. Furthermore, the streak camera is operated with a predetermined timing in accordance with the timing that the monitor light is emitted.

As a laser used for the laser beam source device 111, it is possible to use, e.g., a ruby laser, a yttrium aluminium garnet (which will be referred to as a "YAG" hereinafter) laser, an excimer laser and others.

The laser beam source device 111 is a pulse oscillation type laser beam source device, and usually generates a laser beam EX having an energy of approximately 1 J per pulse with a pulse time of 20 to 100 nano-seconds (which will be referred to as "ns" hereinafter). In the example shown in FIG. 1, a krypton fluorine (which will be referred to as "KrF" hereinafter) laser is used as a laser beam source, and a laser beam EX having a pulse width of approximately 25 ns is obtained at a rate of 100 times in one second.

The laser beam source device 111 can select an entire area of a partial area of the thin film F which is a strip-like area of, e.g., 365 mm×400 mm as an irradiation position xy of the laser beam EX in order to anneal the thin film F. Moreover, the entire area of the thin film F can be also irradiated with the laser beam by moving the sample base 121 in one direction by the XY stage drive mechanism while irradiating the strip-like area with the laser beam EX. In this case, one irradiation time of the laser beam EX relative to the thin film F can be set to, e.g., 25 ns.

Although not shown, the laser beam source device 111 includes an oscillator which generates laser oscillation, and a lens system which forms a beam shape of the laser beam emitted from the oscillator into a shape appropriate for annealing (laser irradiation). The energy density of the laser with which the thin film is irradiated through the lens system is adjusted to e.g., approximately 1 J/cm$^2$.

As the thin film F, it is possible to use, e.g., an amorphous semiconductor thin film formed to have a predetermined thickness such as a thin film having silicon as a main component, an amorphous silicon hydride thin film, a sputtered silicon thin film, a silicon germanium thin film, a dehydrogenated amorphous silicon thin film. In the example of FIG. 1, a formed amorphous silicon thin film is used. As the amorphous silicon, the dehydrogenated amorphous silicon (a-Si:H) is usually used.

As the substrate S, it is possible to use a transparent glass substrate, a plastic substrate, a silicon substrate or the like. In the example of FIG. 1, a transparent glass substrate is used.

The glass substrate S having the amorphous silicon thin film F is detachably disposed to the sample base 121, and positioned at a position where irradiation of the annealing laser beam EX is possible. In the example of FIG. 1, the amorphous silicon thin film F and the glass substrate S are only partially shown.

The thin film characteristic determination apparatus 1 includes a monitor light irradiator 3, a reflected light measurement device 5 and a signal processor 7.

In the thin film characteristic determination apparatus 1 shown in FIG. 1, the monitor light irradiator 3 includes a monitor light source device 31, a shaping optical device 33, a beam expander 35 and a condenser lens 37.

The monitor light source device 31 of the monitor light irradiator 3 is, e.g., an Ar laser, a helium neon (which will be referred to as "He—Ne" hereinafter) laser or an Nd:YAG laser and outputs an S-polarized or P-polarized continuous wave laser (which will be referred to as a "CW laser" hereinafter) beam. It is to be noted that the monitor light source device 31 is an Nd:YAG laser which can output a laser beam having a wavelength of approximately 532 nm and can obtain a laser beam having beam diameter of approximately 5 mm with the power of 10 mW in the example of FIG. 1.

The shaping optical system 33 includes, e.g., a rectangular or circular lens, uniforms an intensity distribution at a peripheral part (less than that at a central part) due to a cross-sectional intensity distribution of the laser beam which is a Gaussian distribution in many cases, and forms a cross-sectional shape into a predetermined shape. That is, the intensity of the laser beam at the peripheral part that the intensity distribution is lower than that at the central part is uniformed by the shaping optical system 33. Additionally, the cross-sectional shape is formed into a predetermined shape.

The beam expander 35 is useful to expand a condensing angle of the monitor laser beam from the monitor light source device 31 and increase an angle measurement range and an accuracy when condensing the light by the condenser lens 37.

A cross-sectional shape of the continuous (CW) laser beam from the monitor light source device 31 is formed into a predetermined shape by the shaping optical device 33. In the example shown in FIG. 1, the cross section of the monitor laser beam LM is formed into a substantially circular shape (by the shaping optical device 33).

The cross section of the monitor laser beam LM whose beam spot shape has been formed into a predetermined shape by the shaping optical device 33 is expanded by the beam expander 35 since it is desirable to emit a laser beam that a beam diameter of the monitor light condensed on the substrate S is small and an incident angle (angle range) is large in order to enable incoming radiation to the condenser lens 37 with a large angle range, i.e., increase an accuracy of an angle measurement when entering the condenser lens 37 before the substrate S (set on the sample base 121) is irradiated.

The monitor light LM, i.e., the light whose beam spot has been converted into a substantially circular shape through the shaping optical device 33 and the beam expander 35 and to which a large angle range (spread angle=convergent angle in this case) is given is condensed to the thin film F by the condenser lens 37. In the example shown in FIG. 1, the monitor light LM is condensed to the amorphous silicon thin film F deposited with a predetermined thickness on the substrate S through the glass substrate S set at a predetermined position on the sample base 121.

Further, the reflected light measurement device 5 in the thin film characteristic determination apparatus 1 has a light sensing portion 51 which receives the reflected light LR from the thin film F with respect to the monitor light LM, and a signal output portion 55 which photoelectrically converts the light received by an optical system 53 which leads the reflected light LR to the light sensing portion 51 and the light sensing portion 51 and outputs a predetermined electrical signal. It is to be noted that the optical system 53 converts the reflected light LR entering the light sensing portion 51 from a point (having the divergence) into a parallel beam. That is, the angle distribution when the reflected light LR enters the optical system 53 is maintained. Furthermore, when a reflection mirror 57 is provided between the light sensing portion 51 and an object (substrate S), a degree of freedom when the light sensing portion 51, i.e., the reflected light measurement device 5 is arranged is increased.

As a main part of the reflected light measurement device 5, i.e., the signal output portion 55, it is possible to utilize, e.g., a streak camera which converts the light into electrons and then again converts them into the light as will be described later with reference to FIG. 2A.

Figure 2A:
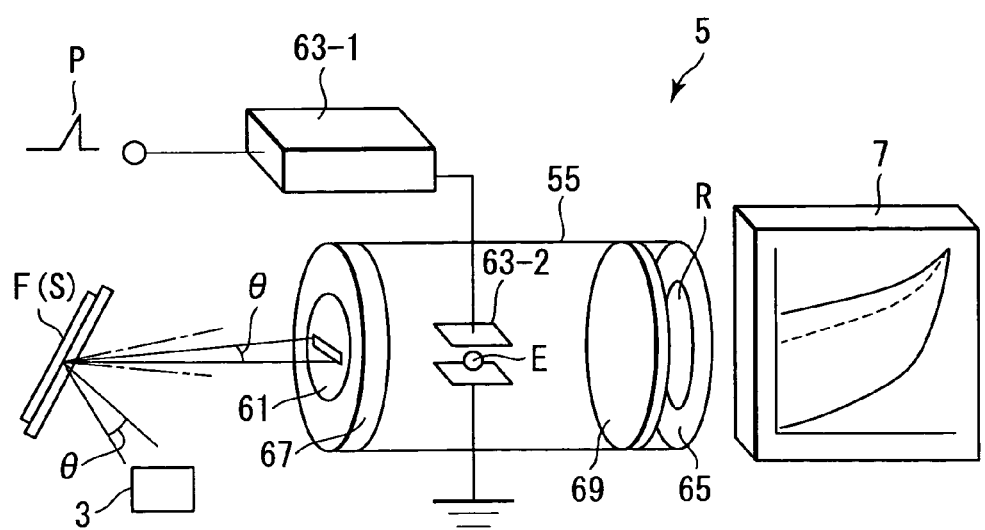
FIG. 2A is a schematic view illustrating an example of the apparatus which determines characteristics of a semiconductor thin film and is incorporated in the substrate finishing/processing apparatus depicted in FIG. 1.

FIG. 2A illustrates an example of the signal output portion, i.e., a streak camera 55 which is incorporated into the apparatus 1 which determines characteristics of the thin film explained in connection with FIG. 1.

The streak camera 55 generally includes a photoelectric converter 61, an electric field generator 63 which generates a sweep electric field, and a fluorescent screen 65. It is to be noted that a sweep voltage (pulse) P is inputted to a sweep electrode 63-2 with a predetermined timing by a sweep circuit 63-1. Moreover, when at least one of an acceleration electrode 67 or an electron multiplier (MCP) 69 is attached to the streak camera (signal output portion) 55, the detection sensitivity can be further improved.

The streak camera 55 is operated with a predetermined timing set by a timing notification mechanism (time adjustment device) 113 illustrated in FIG. 1. For example, an annealing laser beam is outputted from the laser beam source device 111 with a predetermined timing by the timing notification mechanism 113, and an output of the monitor laser beam from the monitor light source device 31 and an operation timing of the streak camera 55 are set with a predetermined timing based on the output of the annealing laser beam by the laser beam source device 111.

Figure 3:
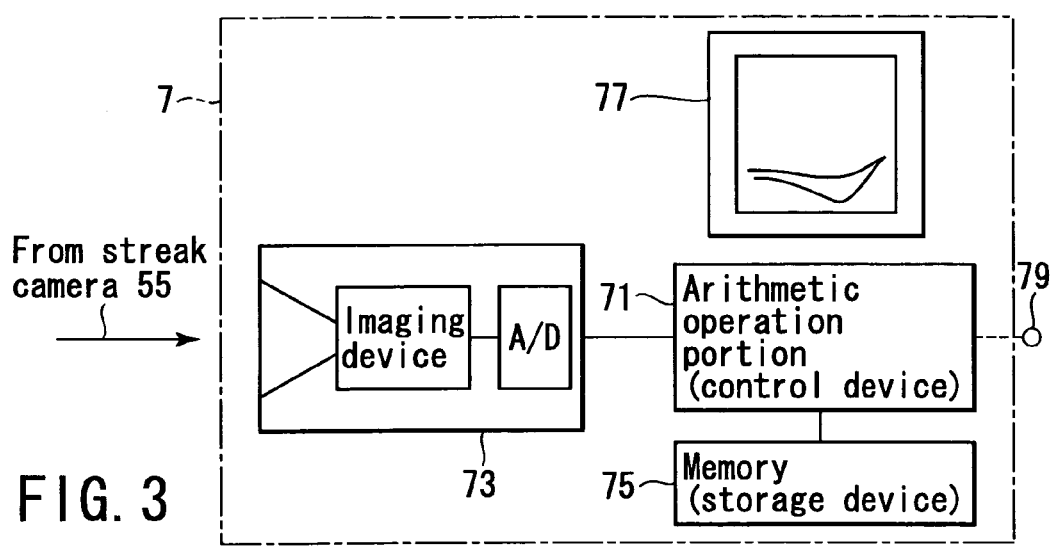
FIG. 3 is a schematic view illustrating an example of signal processing system of the apparatus which determines characteristics of the semiconductor thin film depicted in FIGS. 2A and 2B.

FIG. 3 shows an example of a structure of a signal processing device 7 connected to the thin film characteristic determination apparatus 1 depicted in FIG. 1. As shown in FIG. 3, the signal processing device 7 has a control device 71 which is, e.g., a PC (personal computer), a signal input portion 73, a data storage portion (memory) 75 and a display device 77.

It is to be noted that the signal input portion 73 includes an A/D conversion portion which A/D-converts a position signal corresponding to a position of the light corresponding to an electron E which has reached the fluorescent screen 65 of the streak camera 55, i.e., the light obtained by again converting the electron E which has reached the fluorescent screen 65 into the light at that position by the fluorescent screen 65 and then outputting it, and can sequentially store outputs (position signals) of the streak camera 55 in a memory 75 (data storage portion).

Additionally, a signal output portion 79 may be provided according to needs, and an output from, e.g., a laser device 111 which is a light source of the laser annealing device 101 may be controlled to be fed back based on an output signal from the signal output portion 79.

A description will now be given as to an example of a method which determines characteristics of the thin film by using the apparatus 1 which determines characteristics of the thin film explained in connection with FIGS. 1, 2A, 2B and 3.

First, the substrate S having the thin film F with a predetermined thickness formed thereto is attached at a predetermined position on the sample base 121, and the sample base 121 is moved to a predetermined position by the non-illustrated XY stage drive mechanism.

Then, a KrF laser beam set to the power of approximately 1 J/cm$^2$ per pulse is generated from the laser beam source device 111 with a pulse width of approximately 25 ns for 100 times per second while the sample base 121 is moved in an arbitrary direction at a fixed speed by the XY stage drive mechanism. Therefore, a predetermined position of the thin film F deposited on the substrate S is irradiated with the KrF laser beam for 25 ns. At this moment, since the sample base 121 is moved in an arbitrary direction at a fixed speed, the entire area of the thin film F on the substrate S is exposed by the KrF laser beam in a predetermined order. That is, the entire area of the thin film F on the substrate S is laser-annealed.

A laser beam EX enters the monitor light source device 31 by the timing notification mechanism (time adjustment device) 113 with a predetermined timing relative to generation of the annealing laser beam EX, i.e., substantially simultaneously with output of the laser beam EX, and the monitor light LM is outputted. When an Nd:YAG laser is used for the monitor light source device 31, the monitor light LM is an Nd:YAG laser beam having 10 mW, a beam diameter of approximately 5 mm and a wavelength of approximately 532 nm.

The Nd:YAG laser beam from the monitor light source device 31 is transmitted through the substrate S from a back side of the substrate S via the shaping optical device 33, the beam expander 35 and the condenser lens 37, and condensed to the thin film F. At this time, a condensing diameter of the monitor light LM is condensed (set) so as to be sufficiently small by the condenser lens 37 so that the required angle measurement range and accuracy are satisfied.

At least a part of the monitor light LM with which the amorphous silicon thin film F on the substrate S set on the sample base 121 of a measurement object, i.e., the annealing device 101 is irradiated is returned as the reflected light LR from the amorphous silicon thin film F to the substrate S side.

The reflected light LR returned to the substrate S side is guided in a predetermined direction directed toward the reflected light measurement device, i.e., the streak camera 55 by the reflection mirror 57, and image-formed on the photoelectric conversion surface (photoelectric converter) 61 of the streak camera 55 by the optical system 53. It is to be noted that the characteristics of the thin film F can be detected by measuring a temporal change in an angle distribution of the intensity of the reflected light LR from an output of the streak camera 55 as will be described later and obtaining a temporal change in a refractive index and an extinction coefficient of the thin film F.

The photoelectric converter 61 has a photoelectric surface PS with a strip-like plane shape, and generates electrons E corresponding to the light intensity per surface of the reflected light LR received on the photoelectric surface PS by the photoelectric emission phenomenon on the photoelectric surface PS. Further, the individual electrons E corresponding to the reflected light LR guided to the photoelectric surface PS while holding the angle distribution from the sample surface are attracted to the fluorescent screen 65 in a state that angle information is maintained.

Positions of the electrons E which have been inputted to the photoelectric surface PS of the photoelectric converter 61 and photoelectrically converted are individually measured. Therefore, positional information of the electrons E can be obtained. Since the positional information is associated with, e.g., a fact that a "position" on the outer side means that an "angle" is large, angle information can be finally obtained.

The electric field generator 63 generates an electric field which varies with time. In detail, when a trigger signal P is inputted to a sweep circuit device 63-1, a sweep voltage whose inter-electrode voltage varies with time is inputted from the sweep circuit device 63-1 to an electrode 63-2 with an elapse of time in accordance with the trigger signal P. As a result, a progressing direction of the electrons E generated by the photoelectric converter 61 is changed based on the sweep voltage.

In this case, since a rate of a change in a voltage (inter-electrode voltage) applied to the sweep electrode 63-2 is arbitrarily changed with respect to a predetermined time, a degree of a temporal change of a direction along which the electrons E are guided toward the fluorescent screen 65 (direction along which the electrons E proceed) is arbitrarily determined. In detail, as described with reference to FIG. 2B, a position L to which the electrons E reach is changed by controlling a voltage V applied between the sweep electrode 63-2 and a length d of the sweep electrode 63-2.

Therefore, a position of the electrons E on the fluorescent screen 65 which have been attracted to the fluorescent screen 65 is converted into a temporal change based on a rate of a temporal change that a voltage supplied to the sweep electrode 63-2 is changed, a change distance on the fluorescent surface of the fluorescent screen 65 and a resolution (fluorescent position) of the fluorescent screen (fluorescent position).

For example, assuming that a resolution of the fluorescent screen is 100 μm and an access position L is changed 10 mm with respect to a change in the voltage of one nano-second, the following expression can be achieved.

10 p (pico) sec=1 n (nano) sec×100 μm/10 mm

As a result, the positions of the electrons E guided to the fluorescent screen 65 can be controlled with a high time resolution.

That is, a projection image R having a strip-like plane shape corresponding to the photoelectric surface PS having a strip-like plane shape is formed to the fluorescent screen 65, the access position of the electron E which reaches the fluorescent screen 65 is changed by a variation of the sweep voltage for 1 nsec, and the projection image R having the strip-like plane shape is added so as to follow a change in the voltage. As a result, a plurality of strip-like projection images R are formed on the fluorescent screen 65.

It is to be noted that the projection image R is extracted as image data for each time according to the time resolution by the signal processing portion 7, and a temporal change in the angle distribution of the intensity of the reflected light LR from the substrate S is obtained. Furthermore, a temporal change in the refractive index and the extinction coefficient k of the thin film F deposited on the substrate S is obtained from a temporal change in the acquired angle distribution. The thus obtained temporal change in the refractive index and the extinction coefficient k of the thin film F is displayed as a reflectivity angle distribution in, e.g., a display portion 77.

For example, when the temporal change in the angle distribution of the intensity of the reflected light LR is reduced and the angle distribution of the intensity of the reflected light LR is converged to a fixed or substantially fixed value, solidification of the thin film F is completed (point (condition) that the amorphous silicon thin film is annealed and changed into polysilicon is detected).

As described above, the silicon thin film (amorphous silicon) is molten by laser irradiation with a pulse width of several-ten to 100 nsec, and it is crystallized or crystal grains are grown in a subsequent solidification process for approximately 100 msec. As a result, the silicon thin film converted from the amorphous silicon into the polycrystal silicon can be obtained. That is, a time from melting to end of solidification is several-hundred nxec.

There are known the facts that the extinction coefficient k is increased when the silicon thin film is affected to have further metallic properties by melting and the reflected light intensity is thereby increased and that the extinction coefficient k is decreased due to solidification after melting and the reflected light intensity is thereby reduced.

Based on this, the temporal change in the reflected light intensity of the silicon thin film during melting and solidification is obtained from the temporal change in the angle distribution of the monitor laser beam LM by, e.g., the streak camera 55, thereby monitoring (detecting) the characteristics of the thin film F on the substrate S. That is, the crystallinity (crystal characteristics) of the thin film F on the monitored substrate S can be evaluated in predetermined time units simultaneously with annealing processing using the laser annealing device 101.

It is to be noted that a reflectivity angle distribution at an arbitrary time is displayed in the display portion 77 of the signal processing device 7 as a result of control and signal processing of the control device 71. For example, as a temporal change in the reflectivity angle distribution, the reflectivity of each light beam of the monitor light LM relative to an incident angle $\Phi_0$ to the thin film is displayed in a time series manner. In this case, the reflectivity is a value obtained by dividing the reflected light intensity at each incident angle $\Phi_0$ by the incident light intensity.

As described above, when the temporal change in the angle distribution of the intensity of the reflected light LR from the thin film F on the substrate S is decreased to fall within a predetermined range, the control device 71 (reflected light measurement device 5) of the signal processing portion 7 outputs a signal notifying end of measurement to the time adjustment device 113. That is, when the time adjustment device 113 of the annealing device 110 is informed of end of measurement from the apparatus 1 which determines characteristics of the thin film, the monitor leaser beam LM from the monitor light source device 31 is stopped. It is to be noted that the monitor laser beam LM may be stopped on the assumption that a series of measurement mentioned above is terminated after an elapse of a predetermined time, e.g., 100 ns from start of generation of the monitor light LM, for example.

As described above, according to the apparatus which determines characteristics of the thin film of the present invention, when applying any processing/finishing (e.g., annealing processing) to the thin film, a temporal change in the refractive index n and the extinction coefficient k of the thin film from start of a change (e.g., melting) in the thin film as a processing target to end of the change (e.g., solidification) is obtained with a high time resolution in units of pico seconds, and a progress of a change in state of the thin film (e.g., crystallization) or a transition of growth of the crystal grains can be notified in units of pico seconds based on this. Further, a degree of progress of melting of the thin film or a transition of a temperature of the thin film can be informed.

Furthermore, in FIGS. 1, 2A, 2B and 3, although the description has been given as to the example using the light condensed as the monitor light LM by the condenser lens 37, the light rays (light flux group) generated from a plurality of different light sources may be condensed to one position on the thin film F at different angles in order to obtain the monitor light.

It is to be noted that the time to irradiate the thin film F with the monitor light LM is determined as a time from start of irradiation of the annealing laser beam EX to end of solidification of the thin film F (conversion from the amorphous silicon to the polycrystal silicon) in the above explanation, but of course the monitor light LM may be emitted during irradiation of the annealing laser beam EX.

Moreover, the monitor light LM may be emitted immediately after irradiation of the annealing laser beam EX, i.e., immediately before the thin film F which has been molten by irradiation of the laser beam EX is solidified, and the monitor light LM may be kept being emitted until the molten thin film F is completely solidified (when a predetermined time is elapsed after the reflected light angle distribution does not fluctuate or a fluctuation cannot be detected).

Alternatively, the monitor light LM may be emitted simultaneously with end of irradiation of the annealing laser beam EX, and the monitor light LM may be kept being emitted until end of solidification of the thin film F or for a predetermined time, e.g., 100 ns.

Additionally, when either or both of the acceleration electrode 67 which supplies an acceleration electric field to the electrons E advancing toward the sweep electrode 63-2 and the electron multiplier 69 as typified by an MCP (microchannel plate) which multiplies the electrons which has passed through the sweep electrode 63-2 are incorporated in order to correctly and efficiently image-form the electrons E converted on the photoelectric surface PS onto the fluorescent screen 65, the detection sensitivity is further improved as described above. It is to be noted that the MCP (electron multiplier) 69 has a structure that a metal plate having, e.g., a plurality of holes formed thereto is insulated by an insulating material and such metal plates are laminated, and amplifies the electrons E outputted from the a photoelectric surface 215 by a secondary electron emission caused by the electrons E passing through the opened holes on the metal plates while coming into contact with inner walls of the plurality of holes when a predetermined electric field is applied between the metal plate on the photoelectric converter 61 side and the metal plate on the fluorescent plate 65 side.

Figure 4:
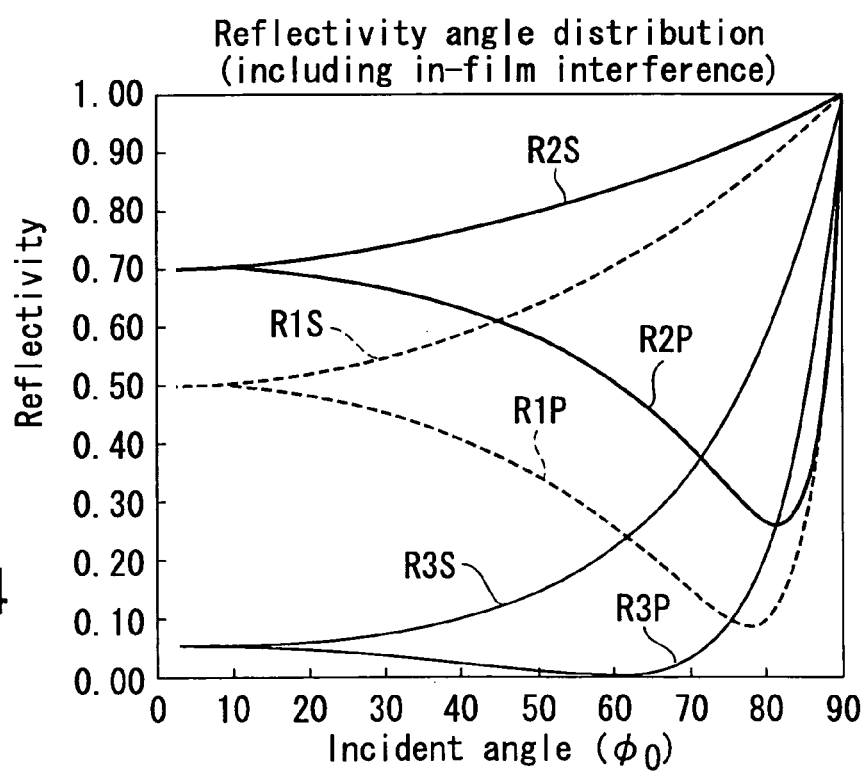
FIG. 4 is a graph illustrating an example of a reflectivity angle distribution of an inspection target obtained by the apparatus which determines characteristics of the semiconductor thin film illustrated in FIGS. 2A, 2B and 3.

FIG. 4 shows an example of the reflectivity angle distribution obtained by the streak camera 55. Curves R1S, R2S and R3S respectively indicate reflectivity angle distributions relative to S polarization in the time series manner. Further, curves R1P, R2P and R3P respectively indicate reflectivity angle distributions with respect to the amorphous silicon thin film before the annealing processing. Furthermore, curves R2S and R2P indicate the reflectivity angle distributions with respect to the molten silicon thin film. Moreover, curves R3S and R3P indicate the reflectivity angle distributions with respect to the polycrystal (amorphous silicon is crystallized by annealing) silicon thin film immediately after solidification.

Figure 5:
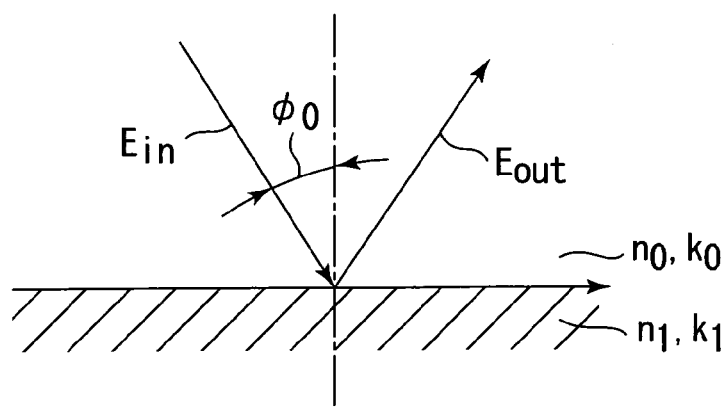
FIG. 5 is a schematic view illustrating an example of a reflectivity angle for creating the reflectivity angle distribution shown in FIG. 4.

When R3P is in contact with the horizontal axis, that means total reflection. As shown in FIG. 5, in regard to the reflectivity $R=E_{out}/E_{in}$, when the light enters toward a layer having a refractive index $n_1$ and an extinction coefficient $k_1$ from a layer having a refractive index $n_0$ and an extinction coefficient $k_0$ with an angle $\phi_0$. In detail, when the light enters the layer having the refractive index $n_1$ and the extinction coefficient $k_1$ from the layer having the refractive index $n_0$ and the extinction coefficient $k_0$ with the incident angle $\phi_0$, assuming that f is a function with respect to each of a P polarization component Rp and an S polarization component Rs, the following expression can be achieved.

$Rp=f(\phi_0, n_0, k_0, n_1, k_1)$ $Rs=f(\phi_0, n_0, k_0, n_1, k_1)$

Therefore, if $\phi_0$, $n_0$, $k_0$ are known, Rp and Rs can be obtained (assuming that $n_0$ and $k_0$ are atmospheric air, "$n_0=1$, $k_0=0$" can be obtained. If $k_1=0$, Rp is theoretically "0" in a case of a specifical incident angle $\phi_0$) based on the following expression.

$Rp=f(n_1, k_1)$ and $Rs=f(n_1, k_1)$

Figure 6:
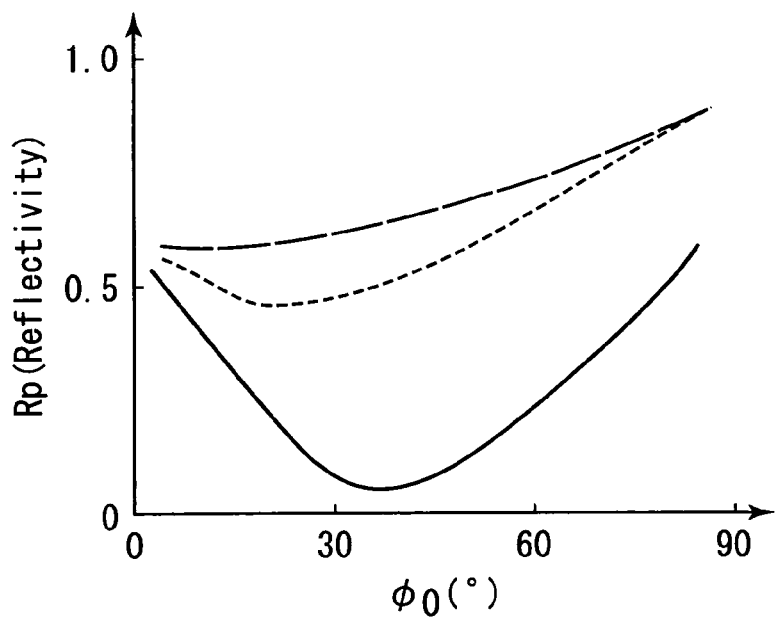
FIG. 6 is a schematic view illustrating an embodiment of the characteristics of the P polarized in which the reflectivity angle distribution shown in FIG. 4.
Figure 7:
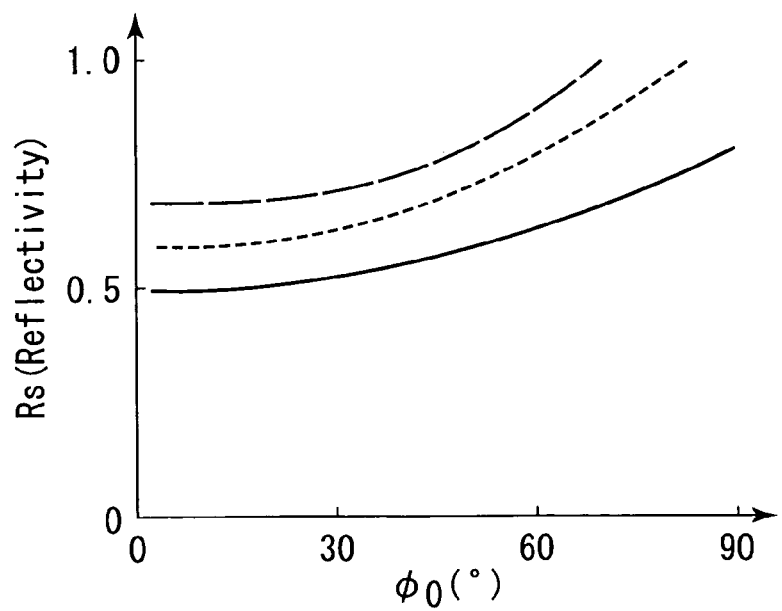
FIG. 7 is a schematic view illustrating an embodiment of the characteristics of the S polarized in which the reflectivity angle distribution shown in FIG. 4.

It is to be noted that Rp has a minimum value (minimal value) with respect to a change in the incident angle $\phi_0$ in many cases as described below in connection with FIGS. 6 and 7 (see FIG. 6). On the other hand, Rs is monotonously increased (see FIG. 7) and demonstrates many characteristic changes in connection with a material or a combination of $n_1$ and $k_1$ when the incident angle $\phi_0$ is increased. Further, when the incident angle $\phi_0$ is changed by using P polarization, an angle with which the reflectivity has a minimum value is a Brewster angle.

However, $f(n_1, k_1)$ obtained from the reflectivity R with respect to arbitrary $n_0$ and $k_0$ is substantially beyond number. Therefore, it is useful to collect data of $n_1$ and $k_1$ as many as possible with a material and a thickness used for the thin film F, and the number of layers in the thin film F being used as parameters.

In order to specify a state of a material by using $n_1$ and $k_1$, a description will now be given as to a primary part of the theory with reference to, e.g., FIGS. 8 to 10.

Figure 8:
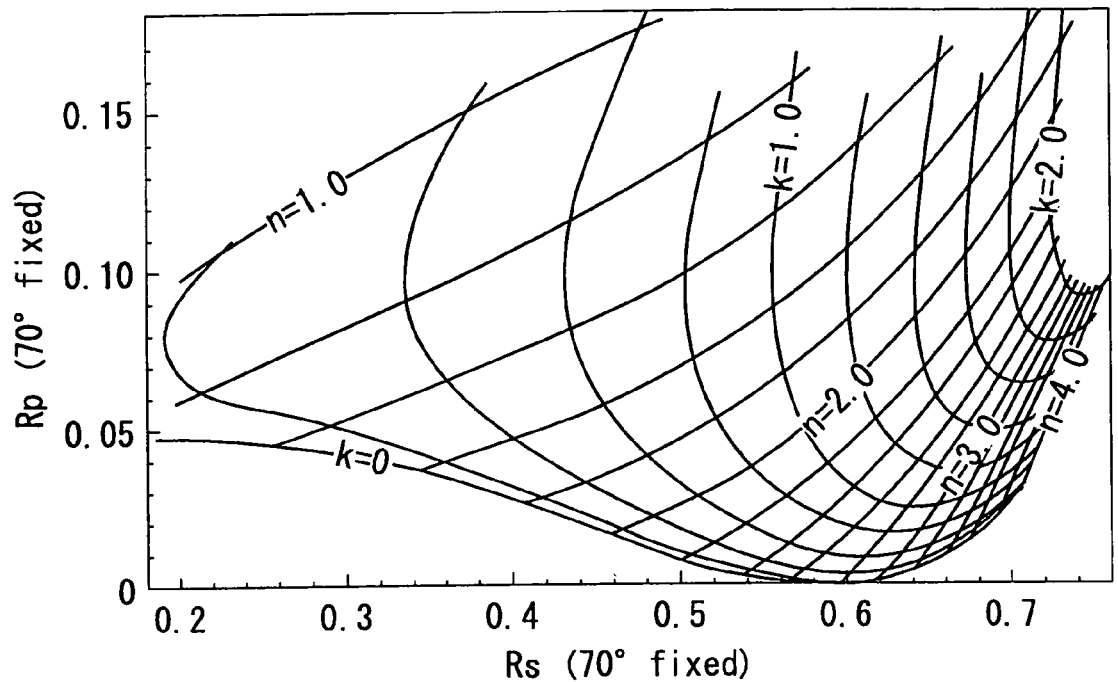
FIG. 8 is a schematic view illustrating an example of a principle for determining the characteristics of the thin film material by using the "$n_1$" and "$k_1$"

For example, FIG. 8 shows many $n_1$ and $k_1$ obtained due to differences in materials when the incident angle $\phi_0$ used to acquire each of Rp and Rs is fixed in relation to an arbitrary material. It can be conceded from FIG. 8 that the reflectivity becomes small as k is small when n if fixed.

Figure 9:
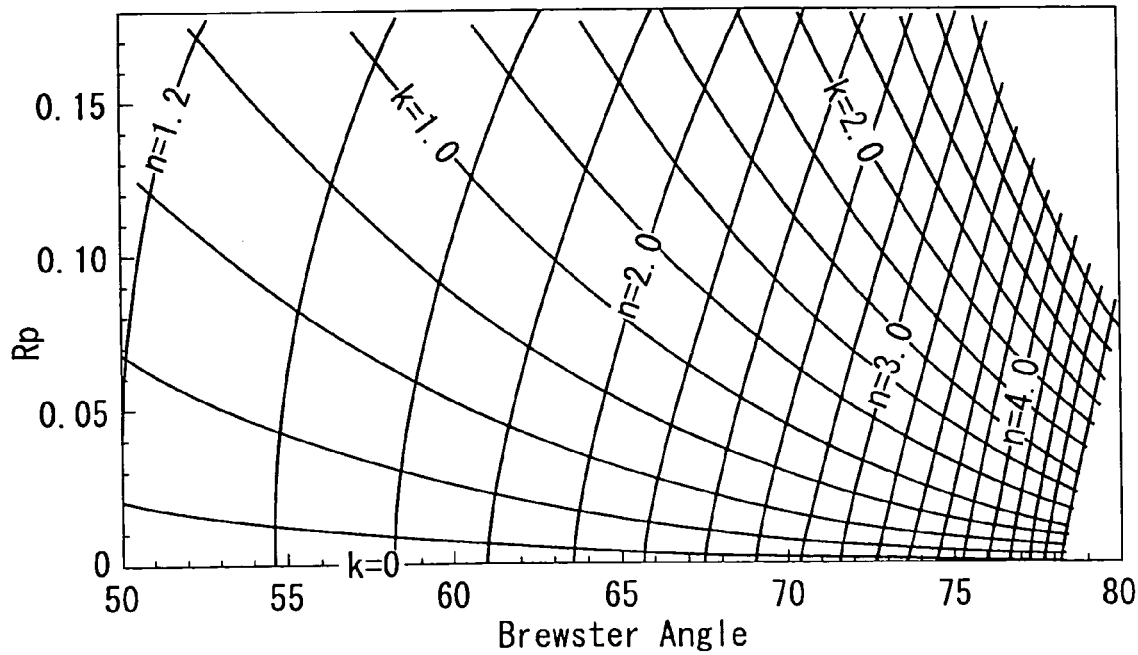
FIG. 9 is a schematic view illustrating an example of a principle for determining the characteristics of the thin film material by using the "$n_1$" and "$k_1$"
Figure 10:
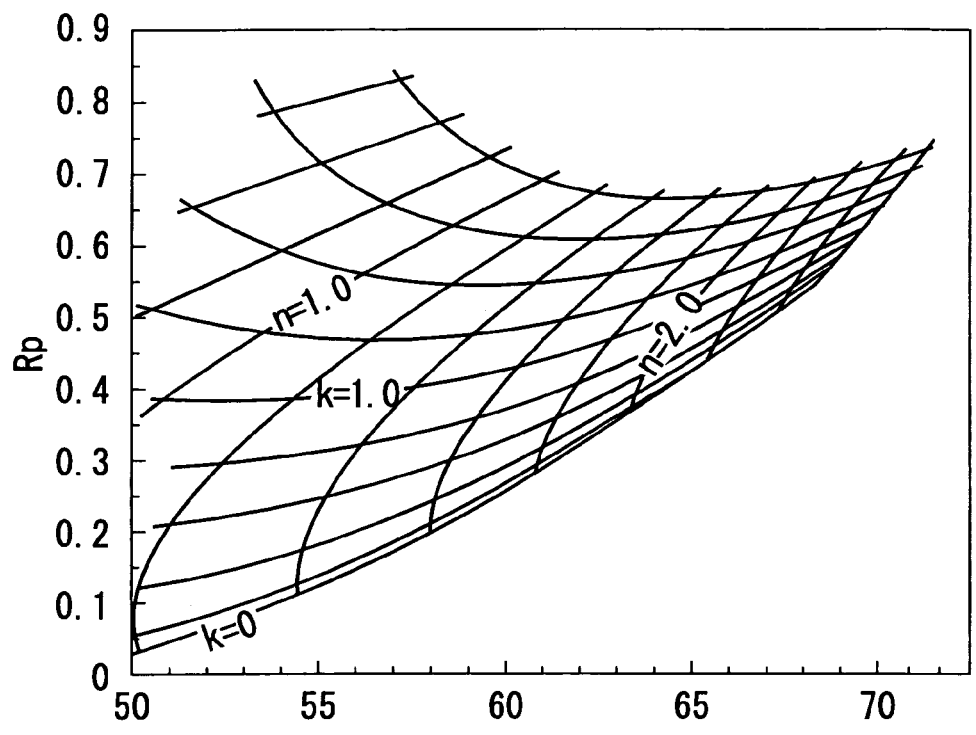
FIG. 10 is a schematic view illustrating an example of a principle for determining the characteristics of the thin film material by using the "$n_1$" and "$k_1$"

FIGS. 9 and 10 show changes in (reflectivity of a P polarization component) Rp and many relationships between $n_1$ and $k_1$ when the horizontal axis indicates the Brewster angle. It can be recognized from FIG. 9 that n is increased as the Brewster angle becomes larger under a condition (material) that the Brewster angle becomes large and that the reflectivity is increased as k become larger when n is fixed to an arbitrary magnitude (value). The same results can be read from FIG. 10. It is to be noted that FIGS. 8 to 10 respectively show data similar to data presented as FIGS. 3 to 5 in "Comparison of Reflection Method for Measuring Optical Constants without Polarimetric Analysis, and Proposal for New Methods based on the Brewster Angle" described in PROC. PHYS. LXXVII, 5, pp. 949 to 957.

By storing data of n1 and k1 in the memory 75 of the signal processing device 7 in this manner, a state of a material can be obtained by using the reflected light.

Incidentally, when using the thin film characteristic determination apparatus 1 and the monitor light source device 31 shown in FIG. 1, it is easy to imagine that the thin film F is in a state that a plurality of layers are laminated. Therefore, it is needless to say that data of various kinds of $n_1$, $k_1$, $n_2$, $k_2$, ... $n_n$, $k_n$ obtained under the condition that the number of layers and the thickness of the layers are changed is stored in the memory 75.

Incidentally, in the above-described thin film characteristic determination apparatus, by calculating a temporal change in the refractive index n and the extinction coefficient k of the thin film taking a thin film other the thin film as an evaluation target formed (positioned) in a layer form above and below the molten silicon film or at least one side of the same or the refractive index and the extinction coefficient of the (simplicial) substrate into consideration, it is possible to accurately know a degree of progress of crystallization of the thin film as the evaluation target or a transition of growth of the crystal grains. Furthermore, in the above-described embodiment according to the present invention, although the description has been given as to the structure and the operation of the thin film characteristic determination apparatus which is incorporated into the laser annealing device as an example, a process that the thin film F is deposited, i.e., a film formation status or the like can be monitored by incorporating the apparatus in, e.g., a sputtering device or a CVD (Chemical Vapor Deposition) device which deposits the thin film F with a predetermined thickness on the substrate S. Moreover, an end point of etching can be detected (monitoring of an etching status of a boundary portion) by incorporating the apparatus in, e.g., a dry etching device or a plasma etching device.

Figure 2B:
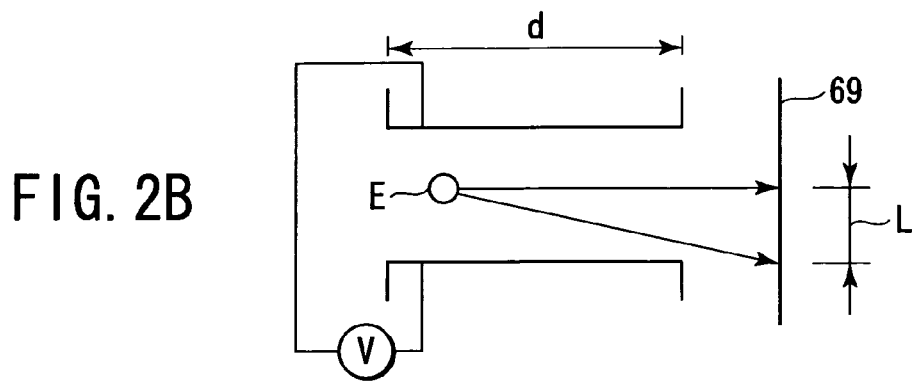
FIG. 2B is a schematic view illustrating an example of operation of a streak camera incorporate with the determining apparatus shown in FIG. 2A.
Figure 11:
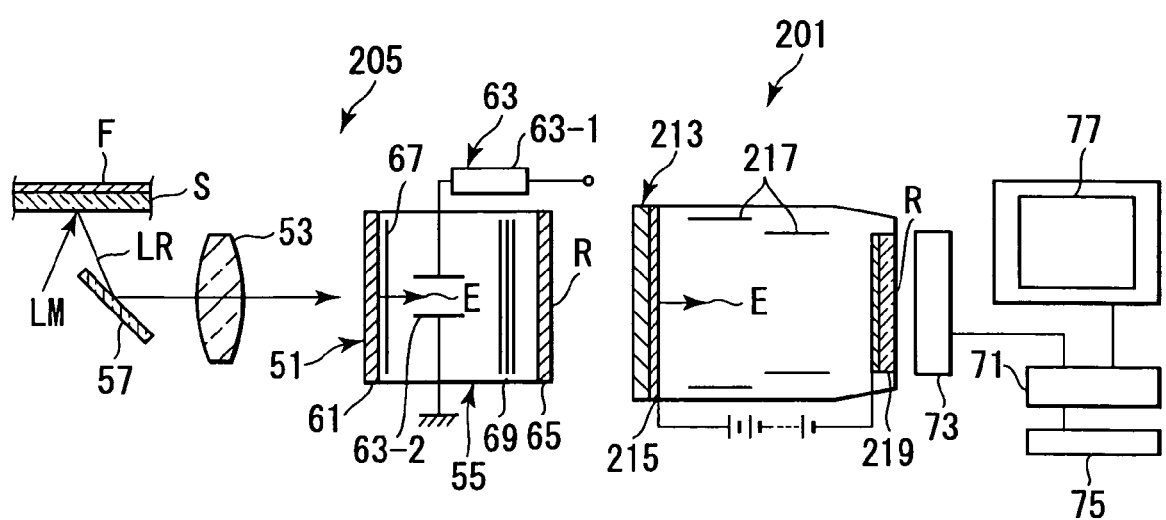
FIG. 11 is a schematic view illustrating another embodiment of the apparatus which determines characteristics of the semiconductor thin film depicted in FIGS. 2A, 2B and 3.

FIG. 11 shows an example of another embodiment of the semiconductor thin film characteristic determination apparatus depicted in FIGS. 2A, 2B and 3. It is to be noted that like reference numerals denote structures equal or similar to those depicted in FIGS. 2A, 2B and 3, thereby eliminating the detailed explanation.

A thin film characteristic determination apparatus 201 shown in FIG. 11 includes a monitor light irradiator 3, a reflected light measurement device 205 and a signal processing device 7.

In FIG. 11, the reflected light measurement device 205 has an image intensifier (light amplifier) 211 which receives a weak input energy, e.g., a near infrared light ray or a near ultraviolet light ray corresponding to a visible light ray or a spectral band close to a visible light ray, photoelectrically converts it, multiplies electrons E obtained by the photoelectric conversion by application of an acceleration electric field and/or an electron multiplier, and then again obtains the visible light ray (from the electrons) by using a fluorescent screen, the image intensifier 211 being provided on a rear stage of the signal output portion described in connection with FIGS. 2A and 2B, i.e., a streak camera 55 between the streak camera 55 and a signal input portion 73 (see FIG. 3) including an imaging device.

It is to be noted that the image intensifier 211 generally includes an input window 213 to which an input light ray or energy is inputted, a photoelectric surface 215 which is formed integrally with the input window 213 and converts the input light or the incident energy inputted from the input window 213 into electrons E, an acceleration electrode 217 which accelerates the electrons E obtained by converting the light or the energy by the photoelectric surface 215, a fluorescent screen 219 which generates the fluorescence by using the accelerated electrons E, and others. The image intensifier 211 amplifies the light or the incident energy received by the input window, i.e., the photoelectric surface 215 and outputs the light (fluorescence). Additionally, it is needless to say that the detection sensitivity is further improved when the same MCP (electron multiplier) as that described above with reference to FIGS. 2A and 2B are incorporated between the photoelectric surface 215 and the fluorescent screen 219.

Since a fluorescent image in a given time rage measured by the streak camera 55 is amplified by the image intensifier 211, the intensity of the input light obtained as the reflected light mentioned above is amplified.

Figure 12:
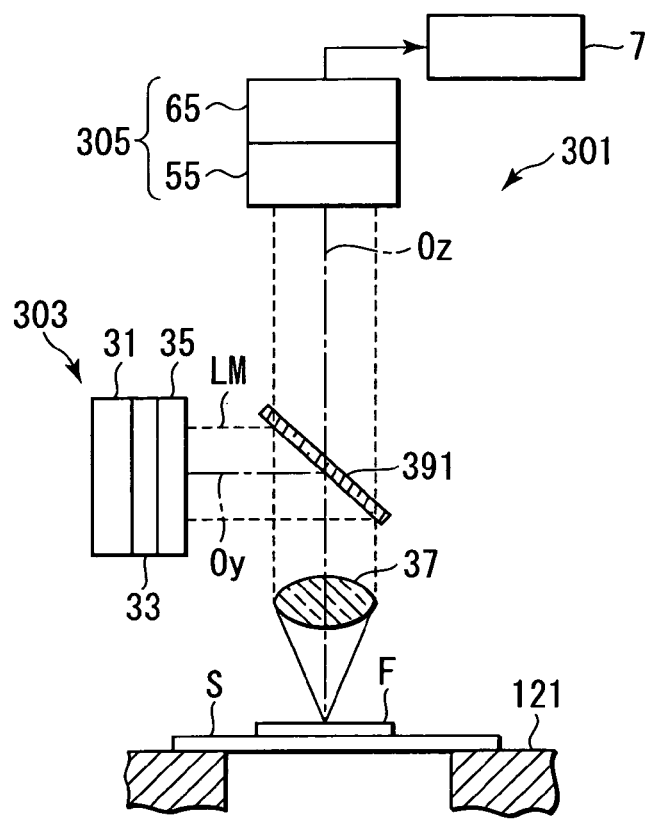
FIG. 12 is a schematic view illustrating another embodiment of the apparatus which determines characteristics of the semiconductor thin film depicted in FIGS. 2A, 2B and 3.

FIG. 12 shows still another embodiment of the thin film characteristic determination apparatus depicted in FIGS. 2A, 2B and 3. It is to be noted that like reference numerals denote structures equal or similar to those shown in FIGS. 2A, 2B and 3, thereby eliminating the detailed explanation.

The thin film characteristic determination apparatus 301 shown in FIG. 12 includes a monitor light irradiator 303, a reflected light measurement device 305 and a signal processing device 7. It is to be noted that the reflected light measurement device 305 is substantially the same as the light measurement device shown in FIGS. 2A, 2B and 3 except that a direction of the light measurement device mentioned above with reference to FIGS. 2A, 2B and 3 is changed, thereby eliminating the explanation. Incidentally, it is needless to say that the image intensifier 211 described in connection with FIG. 11 may be incorporated as the light measurement device.

In FIG. 12, the monitor light irradiator 303 and the reflected light measurement device are provided on the side where the thin film F is deposited, i.e., the side opposite to a sample base 121 with respect to the thin film F deposited with a predetermined thickness on a substrate S placed at a predetermined position on the sample base 121 set on a non-illustrated XY stage drive mechanism. It is to be noted that the reflected light measurement device 305 is provided at a position opposed to the sample base 121, i.e., the substrate S and the thin film F, which is a predetermined position on an optical axis (optical axis of a system) Oz extending from a condenser lens 37 to the reflected light measurement device 305. Further, the monitor light irradiator 303 is inserted at a predetermined angle (generally 45°) with respect to the optical axis Oz. It is arranged in a direction which is substantially parallel to a surface direction of the substrate S positioned on the sample base 121 by, e.g., a beam splitter 391 like a half mirror (the monitor light irradiator 303 is provided at a predetermined position on an optical axis Oy orthogonal to the optical axis Oz).

Additionally, by measuring the reflectivity angle distribution using at least one of the S polarization component light LM output from the light source (laser device) for the monitor light source 303. Since, at least one of the reflectivity of the S polarization component can be simultaneously obtained, and n (refractive factor) and k (extinction coefficient) (which are used to specify a condition of the substrate) can be further accurately measured.

Figure 13:
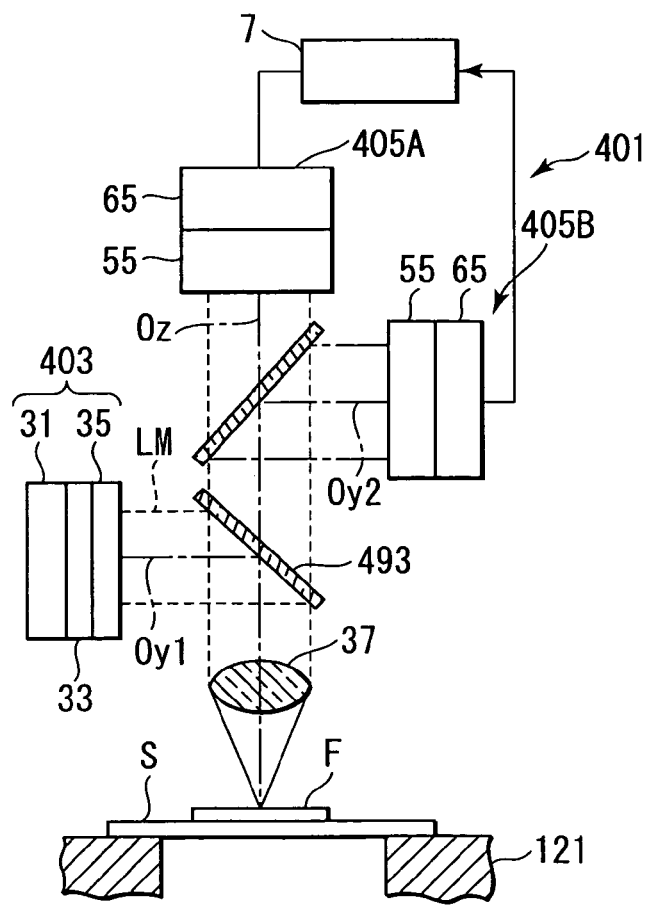
FIG. 13 is a schematic view illustrating still another embodiment of the apparatus which determines characteristics of the semiconductor thin film depicted in FIGS. 2A, 2B and 3.

FIG. 13 shows further another embodiment of the thin film characteristic determination apparatus depicted in FIG. 12. Like reference numerals denote structures equal or similar to those illustrated in FIG. 12, thereby eliminating the detailed explanation. Furthermore, in FIG. 13, a light source is a polarization light source, and an object is to simultaneously measure the respective reflected light rays having a P polarization component and an S polarization component by using two photo detectors.

The thin film characteristic determination apparatus 401 shown in FIG. 13 includes a monitor light irradiator 403, first and second reflected light measurement devices 405A and 405B, and a signal processing device 7. It is to be noted that the monitor light irradiator 403 is the same as that described above in connection with FIG. 12, thereby eliminating the explanation. Incidentally, it is needless to say that each of the reflected light measurement devices 405A and 405B may be a measurement device in which the image intensifier mentioned above with reference to FIG. 11 is incorporated.

In FIG. 13, the monitor light irradiator 403 and the first and second reflected light measurement devices 405A and 405B are provided on a side where the thin film F is deposited, i.e., a side opposite to a sample base 121 with respect to the thin film F deposited with a predetermined thickness on a substrate S placed at a predetermined position on the sample base 121 set on a non-illustrated XY stage drive mechanism.

The first reflected light measurement device 405A is provided at a position opposed to the sample base 121, i.e., the substrate S and the thin film F, which is a predetermined position on an optical axis (optical axis of a system) Oz extending from a condenser lens 37 toward the first reflected light measurement device 405A. Furthermore, the second reflected light measurement device 405B is provided at a position opposed to the sample base 121, i.e., the substrate S and the thin film F, which is a predetermined position in a direction orthogonal to the optical axis Oz. It is to be noted that the second reflected light measurement device 405B is inserted at a predetermined angle (generally 45°) with respect to the optical axis Oz. It is arranged in a direction substantially parallel to a surface direction of the substrate S positioned on the sample base 121 through, e.g., a beam splitter 492 such as a half mirror (the second reflected light measurement device 405B is provided at a predetermined position on an optical axis $Oy_2$ orthogonal to the optical axis Oz).

On the other hand, the monitor light irradiator 403 is inserted at a predetermined angle (generally 45°) with respect to the optical axis Oz. It is arranged in a direction substantially parallel to the surface direction of the substrate S positioned on the sample base 121 through, e.g., a beam splitter 493 such as a half mirror (monitor light irradiator 403 is provided at a predetermined position on an optical axis $Oy_1$ orthogonal to the optical axis Oz).

Additionally, by measuring the reflectivity angle distribution in directions orthogonal to each other by using the polarization light source (laser device) for the monitor light source 403, the reflectivities of the P polarization component and the S polarization component can be simultaneously obtained, and n (refractive factor) and k (extinction coefficient) (which are used to specify a condition of the substrate) can be further accurately measured.

It is to be noted that, as apparent from FIG. 13, the monitor light irradiator 403 and the second reflected light measurement device 405B are arranged in parallel with the substrate S. Further, the directions of angle distribution of the reflected light LR received by the non-illustrated streak camera included by each of the first and second reflected light measurement devices 405A and 405B can be determined as two axial directions orthogonal to each other by appropriately orientating the direction of the beam splitter 492.

In this case, the reflectivity components of the two axes (i.e., the P polarization component and the S polarization component) can be simultaneously obtained by incorporating, e.g., two-dimensional analysis software (application) in an arithmetic operation portion (control device) 71 of a signal processing portion 7.

Figure 14:
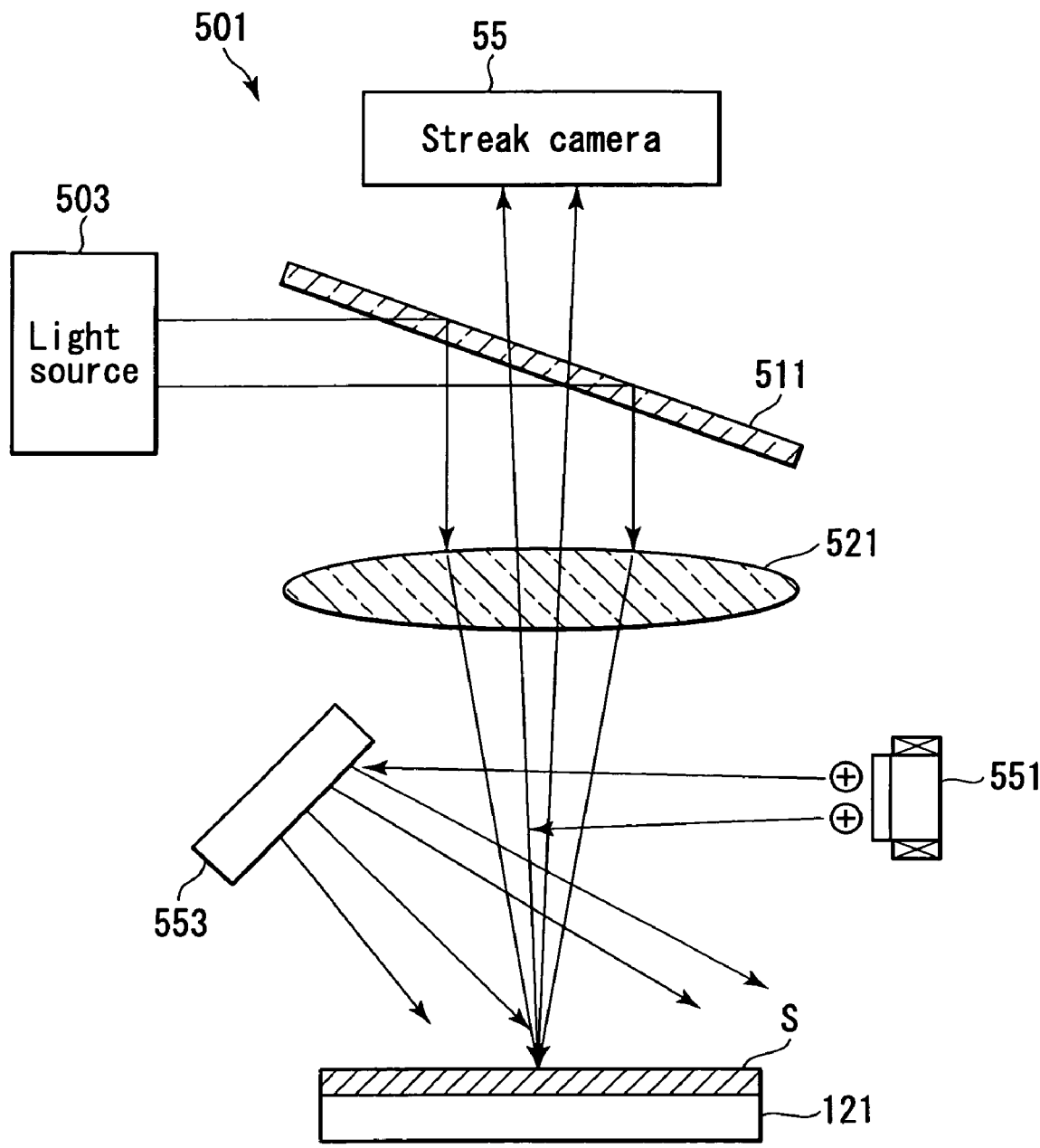
FIG. 14 is a schematic view illustrating further another embodiment of the apparatus which determines characteristics of the semiconductor thin film depicted in FIGS. 2A, 2B and 3.

FIG. 14 shows an example that the thin film characteristic determination apparatus depicted in FIGS. 2A, 2B and 3 is applied to an ion beam sputtering device 501. It is to be noted that like reference numerals denote structures equal or similar to those shown in FIGS. 2A, 2B and 3, thereby eliminating the detailed explanation.

In FIG. 14, for example, an Si thin film with a predetermined thickness is deposited on a substrate S placed at a predetermined position on a sample base 121 set on a non-illustrated XY stage drive mechanism.

An ion beam is provided from an ion source 551 which can emit an ion beam of, e.g., $Ar^+$ ions toward a target 553 which is, e.g., Al. It is to be noted that the ion beam sputtering device is well known, and hence the detailed explanation will be eliminated.

A monitor light irradiation device 503 and a streak camera 55 in the thin film characteristic determination apparatus are provided with, e.g., a lens 505 (or a protection glass with a uniform thickness although not shown) interposed outside a non-illustrated housing (glass container) so as not to be affected by the ion beam.

The monitor light irradiation device 503 is, e.g., a known He—Ne laser and outputs a laser beam with a predetermined wavelength (633 nm).

Like the above description, the monitor light illumination device 503 includes, e.g., a shaping optical system, a beam expander and others, and the laser beam having a predetermined shape and a cross-sectional light intensity given thereto is guided toward the substrate S by a half mirror 511. The laser beam bent by the half mirror 511 is condensed to a predetermined position on the substrate S by, e.g., a condensing optical system 521.

The laser beam reflected by the substrate S, i.e., the reflected light is guided to the streak camera through the half mirror 511.

An output (image) from the streak camera 55 is inputted to a signal processing device 7 as described above with reference to FIG. 3. In the signal processing device 7, reference is made to reflected light data stored in a memory 75 and a change in a state of the thin film provided to the substrate S is monitored.

Moreover, although not described in detail, a glass substrate having formed thereto a TFT pattern (thin film transistor) obtained by a combination of semiconductor patterns formed by providing a resist layer on the substrate (thin film) having a semiconductor thin film formed into a predetermined shape by the thin film characteristic determination apparatus according to the present invention and exposing an optical image transmitted through (MOS-TFT, i.e., a pattern for the thin film transistor) on the surface of the resist layer is opposed to an opposed substrate having a predetermined pattern formed thereto with a predetermined gap therebetween, an electric optical material, e.g., a liquid crystal material with a predetermined thickness is then arranged between the both substrates, and a drive circuit or the like is added with a space between the both substrates being sealed, thereby forming a liquid crystal panel.

As described above, according to the thin film characteristic determination apparatus of the present invention, when applying any processing/finishing (e.g., annealing processing) to the thin film, a temporal change in the refractive index n and the extinction coefficient k of the thin film in a period from start of a change in the thin film as a processing target (e.g., melting) to end of the change (e.g., solidification) can be obtained with a high time resolution of picoseconds, a progress of a change in state of the thin film (e.g., crystallization) or a transition of growth of crystal grains can be notified in pico-second units, and it is also possible to know a degree of a melting progress of the thin film or a transition of a temperature of the thin film.

For example, in laser annealing by which the amorphous silicon is poly-crystallized, when a temporal change in the angle distribution of the intensity of the reflected light obtained by the reflected light measurement device is decreased and the angle distribution of the intensity of the reflected light is converged to a fixed or substantially fixed value, a fact that the thin film is solidified (poly-crystallized) can be detected in ps units (a point (condition) that the amorphous silicon thin film is annealed and changed into polycrystal silicon is detected).

Moreover, by calculating a temporal change in the refractive index n and the extinction coefficient k of the thin film taking a refractive index and an extinction coefficient of a thin film other than the thin film as an evaluation target formed (positioned) above and below the molten silicon film or on at least one side of the same in a layer form and a (simplicial) substrate into consideration, it is possible to further accurately know a progress degree of crystallization of the thin film as the evaluation target or a transition of growth of crystal grains.

Additionally, by measuring the reflectivity angle distribution in directions orthogonal to each other by using the polarization light source (laser device) for the monitor light source, the reflectivities of the P polarization component and the S polarization component can be simultaneously obtained, and n (refractive factor) and k (extinction coefficient) (which are used to specify a condition of the substrate) can be further accurately measured.

The present invention is not limited to the embodiments described above and can be modified in various manners without departing from the spirit and scope of the invention.

For example, the present invention can provide the method for determining characteristics of a semiconductor thin film according to the present invention which is a method for determining characteristics of a semiconductor thin film irradiated with an annealing laser beam, comprising: emitting a monitor light ray which is condensed at a position irradiated with a laser beam during or immediately after irradiation of an annealing laser beam; receiving a reflected light ray of the monitor light from the thin film on a light sensing surface having a plurality of substantially continuous light sensing elements; measuring a temporal change in an angle distribution of an intensity of the reflected light received on the light sensing surface; and calculating a temporal change in a refractive factor and an extinction coefficient of the thin film based on the temporal change in the angle distribution of the intensity of the reflected light.

According to the present invention, since the reflected light of the monitor light from the thin film is received on the light sensing surface having the plurality of substantially continuous light sensing elements, the angle distribution of the reflected light from the thin film can be received at all positions on the light sensing surface at a time.

According to the present invention, the angle distribution of the intensity of the reflected light is acquired as a continuous distribution in place of a discrete distribution, thereby determining a refractive index or an extinction coefficient which are important to evaluate a progress degree of crystallization of the thin film. At this time, since the reflected light is received on all of the light sensing surface at a time, the reflected light entering the light sensing surface can be identified with a high time resolution, and a temporal change in the angle distribution of the reflected light that the intensity is continuously changed in a very short time in melting and solidification processes of the thin film can be measured with a high time resolution. That is, a progress degree of crystallization of the thin film in the melting/solidification processes of the thin film can be evaluated every very short time.

According to the present invention, the light sensing surface is determined as a photoelectric surface having a strip-like plane shape. The reflected light which has entered the photoelectric surface is converted into electrons by a photoelectric conversion phenomenon on the photoelectric surface. As a result, the reflected light is detected as one or more electrons, detection with the size of the electrons, i.e., detection with the very high spatial resolution is enabled, the reflected light can be detected with a high time resolution corresponding to this spatial resolution, and a progress degree of crystallization of the thin film can be evaluated every very short time.

According to the present invention, measurement of a temporal change in the angle distribution of the intensity of the reflected light is performed by generating electrons corresponding to the reflected light received on the photoelectric surface and passing the generated electrons through an electric field which varies with time. According to this, spatial position of the individual electrons which are continuously generated in accordance with the reflected light which enters the photoelectric surface in detection of the reflected light are controlled by a temporal change in the electric field. That is, the spatial positions of the generated electrons can be controlled every temporal change in the electric field, e.g., 1 pico-second. That is, it is possible to perform a control with a high time resolution.

What is claimed is:

1. A method for determining characteristics of a thin film, comprising:
    irradiating with a monitor light ray at least a position of a processing target which is irradiated with a light energy which can perform predetermined processing or finishing;
    detecting a reflected light ray generated from the processing target by the monitor light ray by a light sensing mechanism having a plurality of substantially continuous light sensing elements; and
    measuring a temporal change in an angle distribution of an intensity of the reflected light detected by the light sensing mechanism, wherein the light sensing mechanism includes a strip-like fluorescence surface which extends in one arbitrary direction.

2. The method for determining characteristics of a thin film according to claim 1, the measurement of the temporal change in the angle distribution of the intensity of the reflected light is to generate electrons corresponding to the reflected light detected by the light sensing mechanism, guide the generated electrons to the fluorescence surface in a strip-like shape extending in one arbitrary direction by an electric field which varies with time, and obtain data for each time acquired on the fluorescence surface.

3. A method for determining characteristics of a thin film, comprising:
    irradiating with a monitor light ray at least a position of a processing target which is irradiated with a light energy which can perform predetermined processing or finishing;
    detecting a reflected light ray generated from the processing target by the monitor light ray by a light sensing mechanism having a plurality of substantially continuous light sensing elements;
    measuring a temporal change in an angle distribution of an intensity of the reflected light detected by the light sensing mechanism; and
    calculating a temporal change in a refractive index and an extinction coefficient of the processing target based on the measured temporal change in the angle distribution of the intensity of the reflected light ray, wherein the light sensing mechanism includes a strip-like fluorescence surface which extends in one arbitrary direction.

4. The method for determining characteristics of a thin film according to claim 3, the measurement of the temporal change in the angle distribution of the intensity of the reflected light is to generate electrons corresponding to the reflected light detected by the light sensing mechanism, guide the generated electrons to the fluorescence surface in a strip-like shape extending in one arbitrary direction by an electric field which varies with time, and obtain data for each time acquired on the fluorescence surface.

5. The method for determining characteristics of a thin film according to claim 4, wherein the data is indicated based on the refractive index and the extinction coefficient.

6. An apparatus for specifying a processing state and/or a finishing state of a processing target, comprising:
   a monitor light generation device which can irradiate with a monitor light ray at least a position of a processing target which is irradiated with a light energy which can perform predetermined processing or finishing;
   a light sensing mechanism which detects a reflected light ray generated from the processing target irradiated with the monitor light ray, and detects electrons corresponding to the reflected light ray and/or a light ray obtained by converting the electrons corresponding to the reflected light ray; and
   a reflected light measurement mechanism which measures a temporal change in an angle distribution of an intensity of the reflected light ray detected by the light sensing mechanism, wherein the reflected light measurement mechanism includes a streak camera.

7. An apparatus for specifying a processing state and/or a finishing state of a processing target, comprising:
   a monitor light generation device which can irradiate with a monitor light ray at least a position of a processing target which is irradiated with a light energy which can perform predetermined processing or finishing;
   a light sensing mechanism which detects a reflected light ray generated from the processing target irradiated with the monitor light ray, and detects electrons corresponding to the reflected light ray and/or a light ray obtained by converting the electrons corresponding to the reflected light ray;
   a reflected light measurement mechanism which measures a temporal change in an angle distribution of an intensity of the reflected light ray detected by the light sensing mechanism; and
   a state specifying device which specifies a state of the processing target based on the temporal change in the refractive index and the extinction coefficient of the processing target calculated by the signal processing mechanism, wherein the reflected light measurement mechanism includes a streak camera.

8. An apparatus for specifying a processing state and/or a finishing state of a processing target, comprising:
   a monitor light generation device which can irradiate with a monitor light ray at least a position of a processing target which is irradiated with a light energy which can perform predetermined processing or finishing;
   a light sensing mechanism which detects a reflected light ray generated from the processing target irradiated with the monitor light ray, and detects electrons corresponding to the reflected light ray and/or a light ray obtained by converting the electrons corresponding to the reflected light ray;
   a reflected light measurement mechanism which measures a temporal change in an angle distribution of an intensity of the reflected light ray detected by the light sensing mechanism; and
   a light multiplication mechanism which multiplies an intensity of the reflected light ray generated from the processing target irradiated with the monitor light ray after this light enters the light sensing mechanism, wherein the reflected light measurement mechanism includes a streak camera.

9. An apparatus for specifying a processing state and/or a finishing state of a processing target, comprising:
   a monitor light generation device which can irradiate with a monitor light ray at least a position of a processing target which is irradiated with a light energy which can perform predetermined processing or finishing;
   a light sensing mechanism which detects a reflected light ray generated from the processing target irradiated with the monitor light ray, and detects electrons corresponding to the reflected light ray and/or a light ray obtained by converting the electrons corresponding to the reflected light ray;
   a reflected light measurement mechanism which measures a temporal change in an angle distribution of an intensity of the reflected light ray detected by the light sensing mechanism; and
   a signal processing mechanism which calculates a temporal change in a refractive index and an extinction coefficient of the processing target based on the temporal change in the angle distribution of the intensity of the reflected light ray measured by the reflected light measurement mechanism, wherein the reflected light measurement mechanism includes a streak camera.

10. An apparatus for specifying a processing state and/or a finishing state of a processing target, comprising:
    a monitor light generation device which can irradiate with a monitor light ray at least a position of a processing target which is irradiated with a light energy which can perform predetermined processing or finishing;
    a light sensing mechanism which detects a reflected light ray generated from the processing target irradiated with the monitor light ray, and detects electrons corresponding to the reflected light ray and/or a light ray obtained by converting the electrons corresponding to the reflected light ray;
    a reflected light measurement mechanism which measures a temporal change in an angle distribution of an intensity of the reflected light ray detected by the light sensing mechanism;
    a signal processing mechanism which calculates a temporal change in a refractive index and an extinction coefficient of the processing target based on the temporal change in the angle distribution of the intensity of the reflected light ray measured by the reflected light measurement mechanism; and
    a state specifying device which specifies a state of the processing target based on the temporal change in the refractive index and the extinction coefficient of the processing target calculated by the signal processing mechanism, wherein the reflected light measurement mechanism includes a streak camera.

11. An apparatus for specifying a processing state and/or a finishing state of a processing target, comprising:
    a monitor light generation device which can irradiate with a monitor light ray at least a position of a processing target which is irradiated with a light energy which can perform predetermined processing or finishing;
    a light sensing mechanism which detects a reflected light ray generated from the processing target irradiated with the monitor light ray, and detects electrons corresponding to the reflected light ray and/or a light ray obtained by converting the electrons corresponding to the reflected light ray;
    a reflected light measurement mechanism which measures a temporal change in an angle distribution of an intensity of the reflected light ray detected by the light sensing mechanism;

a signal processing mechanism which calculates a temporal change in a refractive index and an extinction coefficient of the processing target based on the temporal change in the angle distribution of the intensity of the reflected light ray measured by the reflected light measurement mechanism; and a light multiplication mechanism which multiplies an intensity of the reflected light ray generated from the processing target irradiated with the monitor light ray after this light enters the light sensing mechanism, wherein the reflected light measurement mechanism includes a streak camera.

12. An apparatus for determining characteristics of a semiconductor thin film irradiated with an annealing laser beam, comprising:

a monitor light irradiator which irradiates with a monitor light ray a position irradiated with the laser beam; and a reflected light measurement device which receives a reflected light ray of the monitor light ray from the thin film, has a light sensing surface having a plurality of substantially continuous light sensing elements, and measures a temporal change in an angle distribution of an intensity of the reflected light ray, wherein the light sensing surface includes a fluorescence surface having a strip-like plane shape.

13. An apparatus for determining characteristics of a semiconductor thin film irradiated with an annealing laser beam, comprising:

a monitor light irradiator which irradiates with a monitor light ray a position irradiated with the laser beam;

a reflected light measurement device which receives a reflected light ray of the monitor light ray from the thin film, has a light sensing surface having a plurality of substantially continuous light sensing elements, and measures a temporal change in an angle distribution of an intensity of the reflected light ray; and a signal processing device which calculates a temporal change in a refractive index and an extinction coefficient of the thin film based on the temporal change in the angle distribution of the intensity of the reflected light ray, wherein the light sensing surface includes a fluorescence surface having a strip-like plane shape.

* * * * *